United States Patent
Dib

(10) Patent No.: US 8,790,298 B2
(45) Date of Patent: *Jul. 29, 2014

(54) INFUSION CATHETER TIP FOR BIOLOGICS

(75) Inventor: Nabil Dib, Paradise Valley, AZ (US)

(73) Assignee: Translational Biologic Infusion Catheter, LLC, Gilbert, AZ (US)

(*) Notice: Subject to any disclaimer, the term of this patent is extended or adjusted under 35 U.S.C. 154(b) by 121 days.

This patent is subject to a terminal disclaimer.

(21) Appl. No.: 13/473,988

(22) Filed: May 17, 2012

(65) Prior Publication Data

US 2012/0226225 A1    Sep. 6, 2012

Related U.S. Application Data

(63) Continuation-in-part of application No. 12/563,876, filed on Sep. 21, 2009, now Pat. No. 8,647,311.

(51) Int. Cl.

| A61M 29/00 | (2006.01) |
|---|---|
| A61M 25/00 | (2006.01) |
| A61M 39/08 | (2006.01) |
| A61M 25/10 | (2013.01) |
| A61M 25/01 | (2006.01) |
| A61M 39/10 | (2006.01) |

(52) U.S. Cl.
    CPC ..... *A61M 25/0023* (2013.01); *A61M 2039/085* (2013.01); *A61M 25/1002* (2013.01); *A61M 2025/0183* (2013.01); *A61M 2025/1059* (2013.01); *A61M 2025/1097* (2013.01); *A61M 2206/18* (2013.01); *A61M 25/0071* (2013.01); *A61M 2205/3334* (2013.01); *A61M 25/0075* (2013.01); *A61M 2025/1084* (2013.01); *A61M 39/105* (2013.01)
    USPC ............ 604/96.01; 604/97.01; 604/151; 604/246; 604/257; 604/508; 604/509

(58) Field of Classification Search
    USPC ............ 604/93.01, 96.01, 99.01, 103.11, 604/103.12, 103.13, 131, 151, 177, 246, 604/257–258, 508, 509, 522, 97.01
    See application file for complete search history.

(56) References Cited

U.S. PATENT DOCUMENTS

| 4,608,984 A | 9/1986 | Fogarty |
|---|---|---|
| 5,156,594 A | 10/1992 | Keith |

(Continued)

FOREIGN PATENT DOCUMENTS

WO    2008057370 A2    5/2008

OTHER PUBLICATIONS

PCT International Search Report, Application No. PCT/US2013/040396, May 9, 2013.

*Primary Examiner* — Theodore Stigell
(74) *Attorney, Agent, or Firm* — Nydegger & Associates

(57) ABSTRACT

A system for moving particles suspended in a first fluid, and for infusing them into the stream of a second fluid, includes a catheter with a multi-lumen distal separator. The separator is formed with a plurality of parallel lumens, wherein each lumen has a predetermined diameter. Importantly, the diameter of each lumen is dimensioned to sequentially receive particles therethrough, to prevent the particles from flocculating before they enter the stream of the second fluid. A recollection chamber in fluid communication with the separator allows for reconsolidation of the fluid after leaving the separator and for minimizing the damage caused to the vessel when the fluid exits the catheter. An inflatable balloon, affixed to the outside of the catheter, can be provided to regulate flow of the second fluid and thereby facilitate entry of the particles into the stream of the second fluid and increase retention of particles in targeted tissue.

20 Claims, 3 Drawing Sheets

(56) References Cited

U.S. PATENT DOCUMENTS

| | | | |
|---|---|---|---|
| 5,354,279 A | 10/1994 | Hofling | |
| 6,312,374 B1 | 11/2001 | von Hoffmann | |
| 6,319,248 B1 | 11/2001 | Nahon | |
| 6,394,978 B1 * | 5/2002 | Boyle et al. | 604/103.06 |
| 6,524,302 B2 | 2/2003 | Kelley | |
| 6,579,287 B2 | 6/2003 | Wittenberger | |
| 6,840,920 B2 | 1/2005 | Millerd | |
| 8,647,311 B2 * | 2/2014 | Dib | 604/246 |
| 2002/0188276 A1 * | 12/2002 | Evans et al. | 604/509 |
| 2006/0030814 A1 | 2/2006 | Valencia | |
| 2007/0106208 A1 * | 5/2007 | Uber et al. | 604/65 |
| 2010/0234804 A1 | 9/2010 | Hiejima et al. | |
| 2011/0071496 A1 | 3/2011 | Dib | |

\* cited by examiner

INFUSION CATHETER TIP FOR BIOLOGICS

This application is a continuation-in-part of application Ser. No. 12/563,876, filed Sep. 21, 2009, which is currently pending. The contents of application Ser. No. 12/563,876 are incorporated herein by reference.

FIELD OF THE INVENTION

The present invention pertains generally to infusion systems for introducing particles into a fluid stream. More particularly, the present invention pertains to infusion systems for introducing (infusing) particles of biological matter (e.g. stem cells) into the vasculature of a patient without diminishing the therapeutic effectiveness of the biological matter. The present invention is particularly, but not exclusively useful as a system using a multi-lumen filter that allows particles to enter a lumen of the separator, either individually or in small groupings, for subsequent infusion into the vasculature of a patient.

BACKGROUND OF THE INVENTION

An introduction of particles into the vasculature of a patient requires simultaneously satisfying several different concerns or considerations. Depending on the type of particles involved, a concern of significant importance involves preventing the particles from flocculating, i.e. clumping together, as they are being infused or introduced into the vasculature. This is of particular concern in the case of stem cells which can flocculate, but which are most effective in therapy if left to function either as individual cells or in small groups of cells. An additional benefit of preventing particles from flocculating is the prevention of heart attacks caused when clumps of cells are introduced into the coronary circulatory system. Also, it is possible that the retention rate of stem cells in the heart, or other targeted tissue, will increase when the stem cells are infused while flow is slow when the valve or the balloon might help in reducing blood flow.

In all types of intravascular therapy (i.e. intracoronary, intra-arterial or intravenous), it is always an essential concern that the therapeutic agent (e.g. biologics or drugs) be infused or delivered in a predictably controlled manner. Furthermore, it is important that the therapeutic agent be effectively delivered to a proper destination in the vasculature. All of this involves dosage and delivery rate considerations. Moreover, it requires careful handling of the therapeutic agent to insure it (the therapeutic agent) is not damaged or otherwise compromised during an infusion.

From a mechanical perspective, it is known that the diameter of a fluid passageway is a factor that will affect the rate of fluid flow through the passageway. For protocols where small groups of de-flocculated particles are to be infused into a vessel of a vasculature, the diameter of the passageway must obviously be large enough to individually accommodate the small groups of particles. On the other hand, it must also be small enough to separate and prevent larger groups of particles (cells) from clinging to each other. A consequence of this is that the rate at which particles can be carried through the passageway will be circumscribed by the dimensions of the passageway. A further consequence of this is that, as particles leave the passageway, they are then influenced by the flow of fluid (i.e. blood) in the vessel of the vasculature. Depending on the purpose of the protocol, this may mean that the downstream fluid flow in the vasculature will somehow also need to be regulated.

In light of the above, it is an object of the present invention to provide an infusion system that can effectively introduce only small groups of particles into a fluid flow. Another object of the present invention is to provide an infusion system that coordinates the flow rate of a particle/fluid medium (i.e. a first fluid) with the flow rate of a fluid (i.e. a second fluid) into which the particle/fluid medium is being introduced. Still another object of the present invention is to provide an infusion system that produces a low exit pressure to reduce the impact on a vessel wall caused when fluid exits a catheter and enters the vessel. Yet another object of the present invention is to provide an infusion system that is easy to use, is simple to manufacture and is comparatively cost effective.

SUMMARY OF THE INVENTION

In accordance with the present invention, an infusion system includes an elongated catheter which is formed with a central lumen that extends between the proximal and distal ends of the catheter. Preferably, the catheter is tubular shaped with a smooth, circular, outer surface and, for purposes of description, the catheter defines a longitudinal axis. A source of a fluid medium having particles suspended therein (i.e. a particle/fluid medium) is connected in fluid communication with the proximal end of the catheter, and a separator is connected at the distal end of the catheter. For purposes of the present invention, the separator is provided to prevent the particles from flocculating as they are infused or introduced into a vessel in the vasculature of a patient. As envisioned for the present invention, the particles can be either biologics (i.e. cell, gene or protein) or drugs. And, they can be introduced into the vasculature for intracoronary, intra-arterial, or intravenous therapy.

Structurally, the separator is formed with a plurality of parallel lumens. Thus, with the separator affixed to the distal end of the catheter, each lumen of the separator is individually placed in fluid communication with the central lumen of the catheter. Importantly, each individual lumen is dimensioned to sequentially receive only small groups of particles (i.e. less than ten) therethrough. Specifically, although each lumen can receive several particles at a time, each lumen is sufficiently small to effectively separate particles from clinging to each other as they are received into the lumen. It follows that the system also includes a means for moving the particle/fluid medium through the lumen of the catheter, for further movement of the particles in alignment through individual lumens of the separator. For purposes of the present invention the means for moving this particle/fluid medium can be any such means well known in the pertinent art, such as an IV pole, a syringe, or a pump.

In addition to the separator described above, the system of the present invention also includes a configurable (inflatable) valve, such as a balloon. Specifically, the configurable valve is positioned on the outer surface of the catheter to surround the catheter at a location that is proximal to the separator. Further, the valve is formed with a plurality of apertures that are arranged around the axis of the catheter. The purpose of these apertures is to control the axial movement of a fluid (e.g. blood) past the catheter in a distal direction substantially parallel to the axis of the catheter. This control is preferably provided by an inflator that selectively constricts the apertures of the valve to control the flow rate of fluid through the apertures.

In a preferred embodiment of the present invention, the valve is formed as an annulus that is centered on the axis. With this structure, the annulus has an inner diameter that is affixed to the outer surface of the catheter. The valve also has a substantially non-compliant material positioned on the outer periphery of the annulus that maintains the outer diameter at a predetermined radial distance from the catheter when the valve is inflated into a base configuration. As mentioned previously, the valve can be a balloon as commonly used in the pertinent art, and the balloon can be of any material appropriate for this type of procedure. As examples, the balloon may be nylon, polyethylene, or polyethylene terephthalate (PET). Aside from the non-compliant material, the rest of the annulus is made of a compliant material. Importantly, this compliant material is responsive to the inflator to selectively constrict the apertures. Thus, in operation, an additional inflation of the valve beyond its base configuration substantially maintains the outer diameter at the predetermined radial position, while incrementally constricting the apertures.

Additional features of the present invention include a provision for positioning the catheter in the vasculature over a monorail type guide wire. Also, a fluid flow controller can be provided to meter fluid flow from the source into the central lumen of the catheter at a selected fluid pressure.

Within the context of the present invention, several structural variations are envisioned that will facilitate the infusion of biologics into the vasculature of a patient. These variations can also enhance the diffusion and retention rate of the stem cells, drugs, proteins, or particles by the heart. These include: 1) the creation of a recollection chamber at the distal end of the catheter for establishing a safe and effective fluid infusion velocity for the biologics; 2) the orientation of the proximal (upstream) surface of a separator that will promote separation of biologics from each other prior to their infusion; and 3) an inflatable balloon that will coordinate and control blood flow through the vasculature in cooperation with the infusion of biologics. One additional variation is the use of a butterfly catheter in place of the catheter disclosed previously.

A recollection chamber used during an intravenous or an arterial infusion is provided at the distal end of the catheter and is created by positioning the separator in the central lumen of the catheter at a distance "d" from the distal end of the catheter. With this positioning, the recollection chamber will be substantially tubular, it will have a length "d", and it will have a diameter the same as that of the central lumen. It should be noted that the valve, or balloon, does not extend to this location near the distal end of the catheter.

Insofar as structural variations of the separator are concerned, in an alternate embodiment of the separator disclosed above, the proximal (upstream) surface is slanted at an angle "α" relative to the axis of the catheter. Preferably, the angle "α" will be around 60°, with a consequence that the lumens established by the separator will have different lengths. In one version, the proximal (upstream) surface of the separator will be flat, with the entrance to each lumen angled at the angle "α" from the axis of the catheter. In another version, this surface will have a stepped configuration so that the entrance to each lumen will be perpendicular to the axis of the catheter. For both versions, the distal (downstream) surface of the catheter will be perpendicular to the axis of the catheter.

In combination, the separator and the recollection chamber function to promote and maintain the separation of biologics as they are being safely infused. In particular, the recollection chamber slows the fluid velocity rate of the infusion fluid, after it has been accelerated through the separator. To further maintain safe fluid flow through the vasculature, an inflatable balloon can be attached to the outer surface of the catheter and it can be selectively inflated to coordinate the respective rates of blood flow and fluid infusion.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENTS

Figure 1:
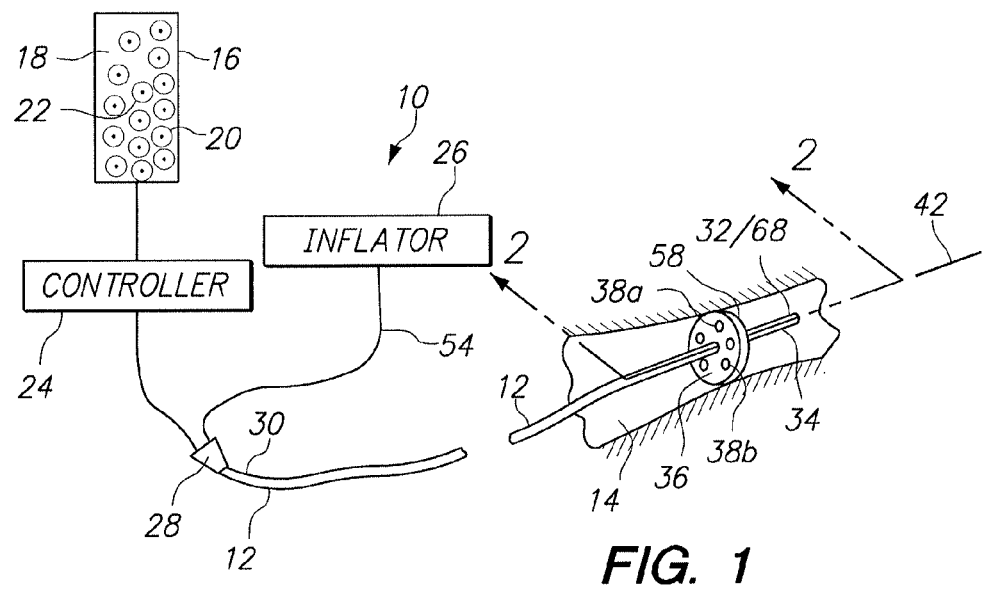
FIG. 1 is a schematic/perspective view of the system of the present invention shown with the system catheter positioned in an operational environment.

Referring initially to FIG. 1 a system for introducing (infusing) a fluid in accordance with the present invention is shown and is generally designated 10. As shown, the system 10 includes a catheter 12 that can be advanced into a vessel 14 to position the catheter 10 at a predetermined location in the vasculature of a patient (not shown). For the purposes of the present invention, the vessel 14 is preferably an artery or a vein in the cardiovascular system of a patient, and the system 10 is used for an intra-arterial, intravenous or intracoronary protocol.

In detail, FIG. 1 shows that the system 10 includes a source 16 for holding a fluid medium 18. As also shown in FIG. 1, a plurality of particles 20 are suspended in the fluid medium 18 to create a particle/fluid medium 22. For the present invention, the particles 20 may be some form of a drug or, most likely, they will be some form of a biologics (i.e. cell, gene or protein). In any event, the particles 20 will be suspended in the particle/fluid medium 22 for transport from the source 16 through the system 10 and into the vessel 14. As mentioned above for the system 10, the source 16 can be a syringe of a type well known in the pertinent art. FIG. 1 also shows that the system 10 includes a controller 24 that is in fluid communication with the source 16. As envisioned for the present invention, the controller 24 can be any type device that is known in the pertinent art for moving a fluid (e.g. the particle/fluid medium 22) through a fluid flow system (e.g. system 10). In general, such a device may be an IV pump, an IV pole, a syringe, or some other fluid flow metering apparatus. For an embodiment of the system 10 wherein the source 16 is a syringe, however, there is no specific need for a controller 24.

FIG. 1 also shows that the system 10 includes an inflator 26 for a purpose to be discussed below. When both the controller 24 and the inflator 26 are used for the system 10, they can be individually joined at a connector 28 to, respectively, establish separate fluid communication channels with the catheter 12. Preferably, as shown, this connector 28 is connected in fluid communication with the proximal end 30 of the catheter 12.

Still referring to FIG. 1, it is seen that the system 10 includes a tip (filter) 32 (hereinafter sometimes also referred to as a separator 68) that is affixed to the distal end 34 of the catheter 12. Further, it is seen that a valve 36 is mounted on the catheter 12 proximal the distal end 34, and that the valve 36 is formed with a plurality of apertures, of which the apertures 38a and 38b are exemplary. The actual construction of the distal portion of the catheter 12, and the cooperation of structure between the separator 68 and the valve 36 will perhaps be best appreciated with reference to FIG. 2.

Figure 2:
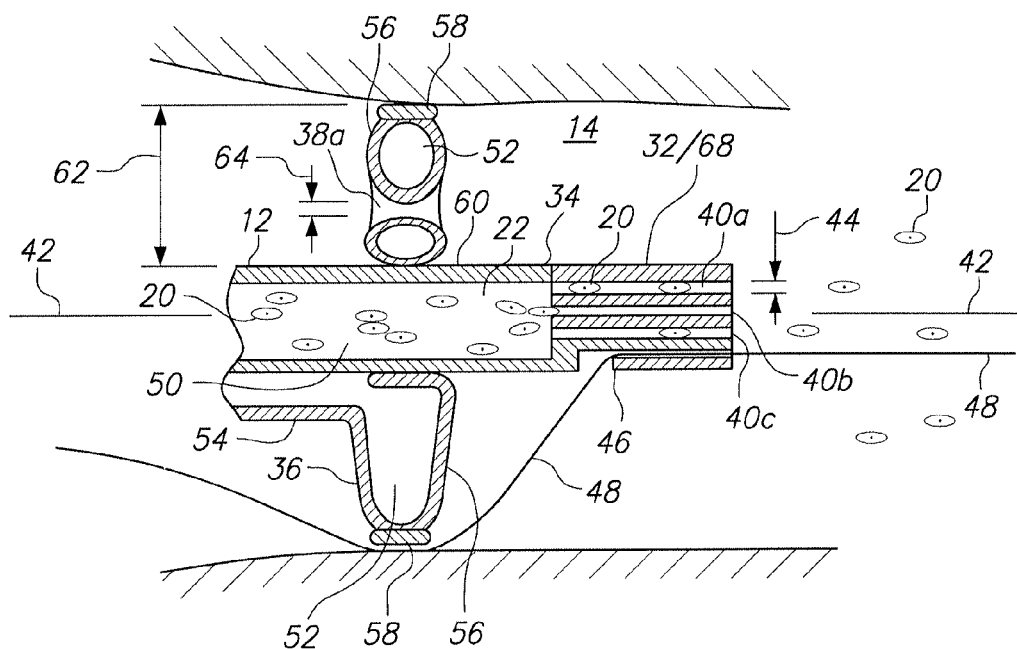
FIG. 2 is a cross section view of the separator and distal portion of the system catheter as seen along the line 2-2 in FIG. 1.

Referring to FIG. 2, and with specific reference to the separator 68, it will be seen that the separator 68 is formed with a plurality of lumens, of which the lumens 40a, 40b, and 40c are exemplary. More specifically, the lumens extend axially through the separator 68 and are substantially parallel to each other. They are also substantially parallel to the axis 42 that is generally defined by the catheter 12. Importantly, each lumen is established with a diameter 44 that is specifically dimensioned to receive only individual or small groups of particles 20. Although each lumen can receive several deflocculated particles 20 at a time, the individual particles 20 or small groups of particles remain separated while they transit the lumen (e.g. see lumen 40a). Further, the separator 68 can be formed with a monorail lumen 46 that will interact with a guide wire 48, in a manner well known by the skilled artisan, for the purpose of positioning the catheter 12 within the vessel 14.

With the structure of the separator 68 in mind, as described above, it is an important aspect of the present invention that the diameter 44 of each lumen be dimensioned to prevent the entry of large groups of flocculated particles 20 into the lumen from the central lumen 50 of the catheter 12. In particular, for different therapeutic protocols, it may be very necessary that the particles 20 be dispersed as they enter the vessel 14, to thereby minimize the possibility of subsequent flocculation in the vessel 14, which may lead to heart attack or stroke if the cells are infused into the coronary circulatory system.

Recall, the valve 36 is formed with a plurality of apertures. Further, with cross reference to FIG. 1 and FIG. 2, it will also be appreciated that, when inflated, the valve 36 is generally shaped as an annulus and is formed with an inflation chamber 52. As shown, the inflation chamber 52 is connected in fluid communication with the inflator 26 via an inflation line 54. Within this structure, the inflation line 54 can be integrated into the catheter 12. For operational purposes, the valve 36 includes a valve body 56 that is made of a compliant, inflatable material. The valve 36 also includes a rim 58 made of a substantially non-compliant material that is located on the periphery of the annulus shaped valve 36. For the system 10, the valve 36 is located proximal to the separator 68, and it is affixed to the outer surface 60 of the catheter 12 by any means known in the pertinent art, such as by gluing or bonding.

Operationally, the valve 36 (balloon) starts from a deflated configuration, and it is then inflated by the inflator 26 into a base configuration (see FIGS. 1 and 2) wherein the valve 36 is constrained by the rim 58. In this base configuration, the valve 36 will extend from the surface 60 of catheter 12 through a radial distance 62 and, in the base configuration, it will most likely make contact with the vessel 14. Also, in the base configuration, each aperture (e.g. aperture 38a) will have a diameter 64. With an additional inflation of the valve 36 by the inflator 26, however, two different structural consequences occur. For one, the rim 58 does not expand from the base configuration. Thus, the radial distance 62 remains substantially constant. For another, the valve body 56 will expand in response to the inflator 26 such that the apertures are incrementally constricted. Stated differently, and with specific reference to the aperture 38a, the diameter 64 will be diminished. In an alternate embodiment for the present invention, there may be no need for the valve 36.

For an operation of the system 10 in an intra-arterial, intravenous or intracoronary protocol, a guide wire 48 is first prepositioned in the vasculature of a patient. The guide wire 48 is then received into the monorail lumen 46 of the catheter 12, and the catheter 12 is advanced over the guide wire 48 and into position in the vasculature of the patient. Once the catheter 12 has been properly positioned, the valve 36 is inflated into its base configuration, or beyond. The exact extent of inflation for valve 36 will depend on the desired flow rate for fluid through the apertures in the vessel 14. With the valve 36 inflated, the controller 24 is then activated to cause a flow of particle/fluid medium 22 from the source 16 and through the central lumen 50 of the catheter 12. As particles 20 in the particle/fluid medium 22 arrive at the separator 68, the respective diameters 44 of individual lumens in the separator 68 allow only individual particles 20 or small groups of particles 20 to enter the lumen. Thus, the flocculation of particles 20 in the central lumen 50 is disrupted, and flocculation of the particles 20 after they have passed through the separator 68 is minimized. Although the above discussion has focused on applications of the system 10 within the cardiovascular system of a patient, the system 10 is appropriate for any use wherein particles 20 may be suspended in a particle/fluid medium 22 for subsequent release as individual particle 20 into a fluid flow (e.g. blood flow through a vessel 14).

Figure 3:
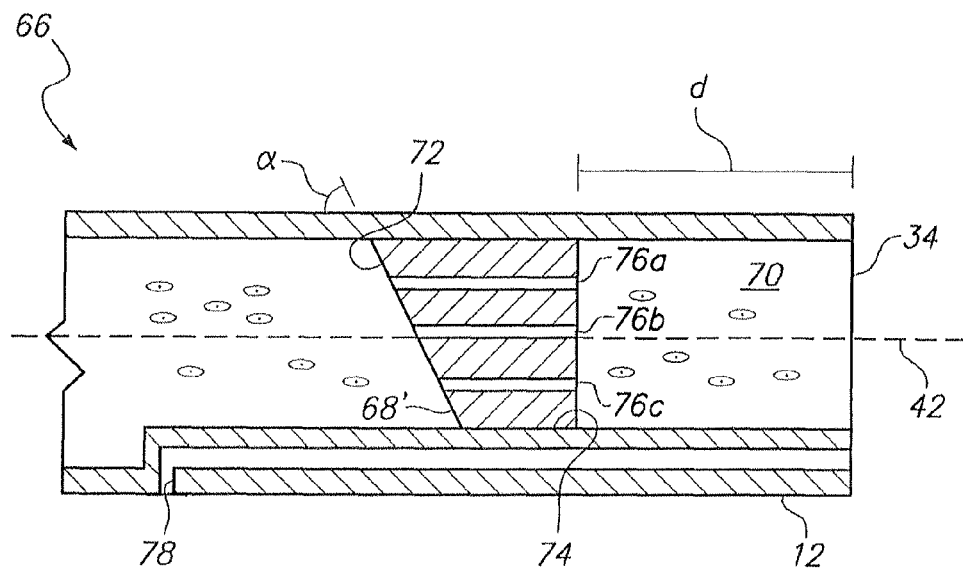
FIG. 3 is a cross section view of an alternate embodiment of the infusion tip as seen along line 2-2 in FIG. 1.

Referring to FIG. 3, an infusion tip for biologics is shown and generally is designated 66. In this embodiment, a separator 68' is located in the central lumen 50 of the catheter 12 at a distance "d" from the distal end 34 of the catheter 12. As so located, the separator 68' creates a recollection chamber 70 having a length "d" at the distal end 34 of the catheter 12. Specifically, the recollection chamber 70 is a tubular section formed onto the distal end 34 of the catheter 12. If necessary, the recollection chamber 70 may be established by a stand-alone piece of tubing that can be attached to the distal end 34 of the catheter 12.

Still referring to FIG. 3, it is seen that the separator 68' has a proximal (upstream) surface 72 and a distal (downstream) surface 74. In detail, the proximal surface 72 of the separator 68' is oriented at a slant angle "α" relative to the axis 42 of the catheter 12. The distal surface 74 of the separator 68', however, is perpendicular to the axis 42, and it is substantially flat. Keeping in mind the structure disclosed above, a consequence of the slanted proximal surface 72 is that the proximal end of each lumen 76a-c will also be slanted at angle "α" relative to the axis 42 of catheter 12. Consequently, when fluid flows through the catheter 12 and encounters the slanted proximal surface 72 of the catheter 12, it is redirected to flow through the lumens 76a-c of the separator 68'. In operation, this redirection helps prevent particles 20 in the fluid from flocculating prior to entering the vasculature of the patient. Upon exiting the lumens 76a-c of the separator 68', the fluid enters the recollection chamber 70 where it is allowed to slow down before entering the vasculature of the patient.

Figure 4:
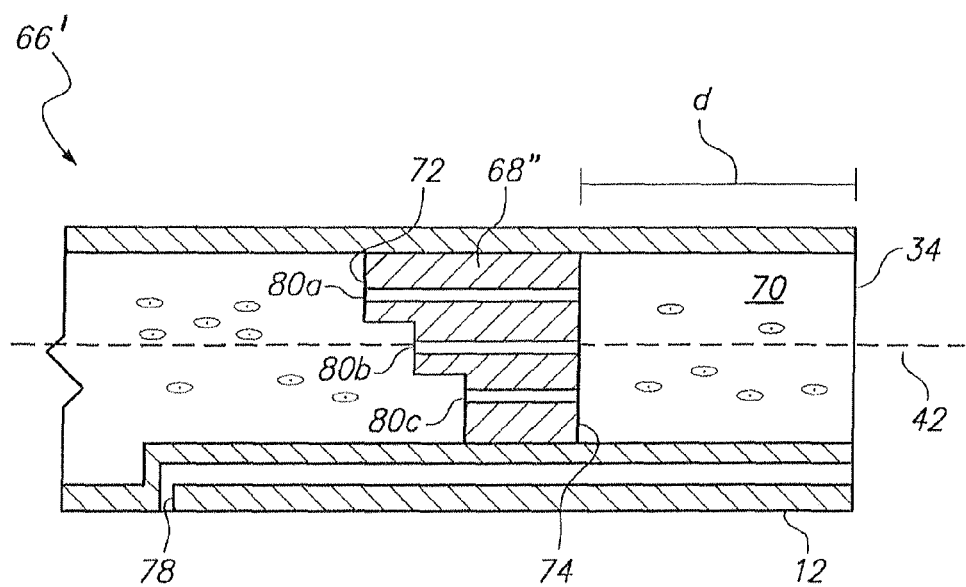
FIG. 4 is a cross section view of an alternate embodiment of the infusion tip shown in FIG. 3.

For embodiments shown in FIGS. 3 and 4, the guide wire exit lumen 78 is formed onto the catheter 12 at a location approximately 25-30 millimeters proximal the separator 68' and 68".

Referring now to FIG. 4, a variation of the infusion tip 66' is shown wherein the proximal surface 72 of the separator 68" is formed with a step configuration. Due to the step configuration, the proximal end of each lumen 80a-c remains substantially perpendicular to the axis 42 of the catheter 12. Thus, in all important respects, the infusion tips 66, 66' shown in FIGS. 3 and 4, respectively, are the same with the exception that the proximal surfaces differ. It should be noted that the proximal surface 72 of the separator 68 can also take the shape shown in FIG. 2 for the separator 32/68.

Figure 5A:
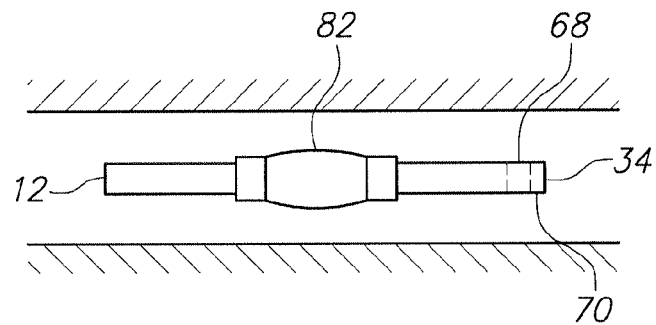
FIG. 5A is a plan view of the balloon of the present invention in a deflated configuration and shown with the catheter positioned in an operational environment.
Figure 5B:
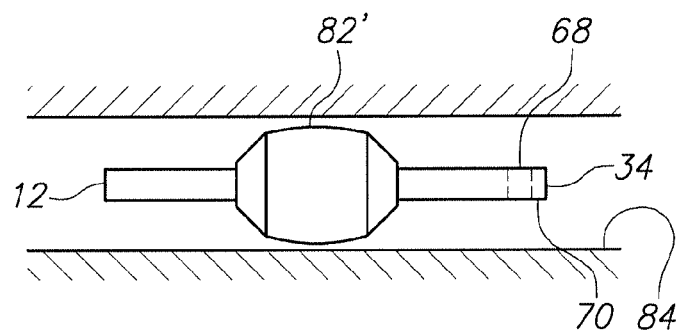
FIG. 5B is a plan view of the balloon of the present invention in an inflated configuration and shown with the system catheter positioned in an operational environment.

Referring now to FIG. 5A and FIG. 5B, a selectively inflatable balloon 82 is shown attached to the catheter 12 at a location proximal the separator 68. When inflated as shown in FIG. 5B, the balloon 82' controls the flow rate of blood around the catheter 12 by expanding radially away from the catheter 12 towards the vessel wall 84. As envisioned for the present invention, the flow rate of the blood outside the catheter 12 should be compatible with the flow rate of fluid inside the catheter 12 in order to minimize turbulence at the distal end 34 of the catheter 12. In any event, the overall objective for the recollection chamber 70 and the inflatable balloon 82 is to decrease the probability of damage or injury to the vasculature of the patient during an infusion by decreasing the flow rate of blood to allow particles additional time to diffuse and to travel through blood vessels and into the tissue to be treated.

Figure 6:
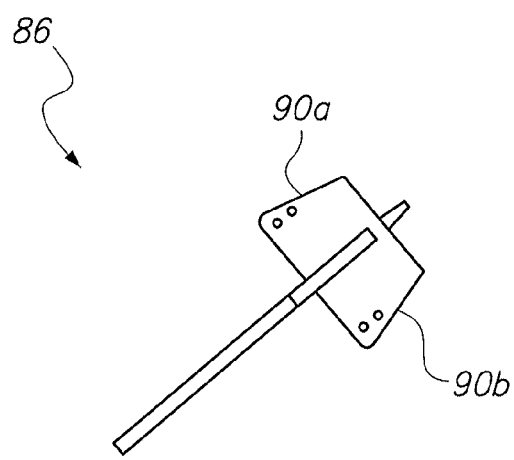
FIG. 6 is a plan view of the butterfly catheter for the present invention.

Referring now to FIG. 6, it is to be appreciated that an infusion tip 66 in accordance with the present invention can be employed in a butterfly catheter 86 of a type that is well-known in the pertinent art. If a butterfly catheter 86 is used, the infusion tip 66 will be essentially the same as disclosed above for other embodiments. The advantage here is that, in appropriate situations, the butterfly catheter 86 may be secured to the patient prior to the release of fluid from the fluid source 16. For example, the wings 90a-b are secured to the patient prior to the release of fluid 18 from the fluid source 16. In all other important respects, the operation of the butterfly catheter 86 with the infusion tip 66 of the present invention is identical to the operation disclosed previously.

While the particular Infusion Catheter Tip for Biologics as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. An infusion system which comprises:
    an elongated catheter formed with a central lumen extending between a proximal end and a distal end;
    a source of a fluid medium having particles suspended therein, wherein the source is connected in fluid communication with the proximal end of the catheter;
    a separator having a proximal end and a distal end formed with a plurality of parallel lumens extending therebetween with each lumen in fluid communication with the central lumen to receive particles from the central lumen, and wherein the separator is positioned in the lumen of the catheter at a distance "d" from the distal end of the catheter to establish a recollection chamber at the distal end of the catheter, and to individually place each lumen of the separator in fluid communication with the central lumen, and wherein each individual lumen is dimensioned to sequentially receive particles therethrough; and
    an infusion device for moving the fluid medium with suspended particles through the central lumen of the catheter, for further movement of the particles in a separated alignment through the individual lumens of the separator for reconstitution of the fluid medium with separated particles in the recollection chamber.

2. A system as recited in claim 1 wherein the catheter has an outer surface and is tubular shaped to define an axis, and wherein the system further comprises:
    an inflatable balloon positioned on the outer surface of the catheter to surround the catheter at a location proximal to the separator; and
    an inflator connected in fluid communication with the balloon for inflating the balloon to selectively control blood flow around the balloon and the outer surface of the catheter.

3. A system as recited in claim 1 wherein the recollection chamber has a length "d" of approximately 1 millimeter (mm).

4. A system as recited in claim 1 further comprising a guide wire selectively engaged with the catheter to position the separator in the vasculature of a patient.

5. A system as recited in claim 4 wherein the catheter is constructed with a guide wire exit port, wherein the exit port is located in a range of 25-30 centimeters (cm) proximal the separator.

6. A system as recited in claim 1 wherein the infusion device for moving the fluid through the catheter is a pump.

7. A system as recited in claim 1 wherein the particles are selected from a group consisting of agents useful for gene therapy, drug therapy and protein therapy.

8. A system as recited in claim 1 wherein the particles are stem cells.

9. A system as recited in claim 1 wherein the catheter is a butterfly catheter comprising a plurality of flexible, interconnected, plastic wings affixed to the proximal end of the catheter.

10. A system as recited in claim 1 wherein the catheter defines an axis and the proximal end of the separator is slanted at an angle "$\alpha$" relative to the axis, with the distal end of the separator being substantially perpendicular to the axis.

11. A system as recited in claim 10 wherein a proximal end of each lumen in the separator is oriented substantially perpendicular to the axis of the separator to establish a step configuration for the proximal end of the separator.

12. A system for introducing particles into the vasculature of a patient, the system comprising:
    an elongated catheter formed with a central lumen extending between a proximal end and a distal end, wherein the catheter defines an axis;
    a source of the particles suspended in a fluid, wherein the source is connected in fluid communication with the proximal end of the catheter;
    a substantially cylindrical shaped separator in fluid communication with the particle source, wherein the separator has a proximal end and a distal end and is formed with a plurality of longitudinally aligned, parallel lumens, with each lumen in fluid communication with the central lumen to receive particles from the central lumen and with each lumen dimensioned to receive particles therethrough, and wherein the separator is positioned in the catheter at a distance "d" from the distal end of the catheter to establish a recollection chamber between the separator and the distal end of the catheter;
    an inflatable balloon positioned around the catheter and affixed thereto, with the balloon extendable in a radial direction outward from the catheter to control blood flow around the catheter in a direction substantially parallel to the axis;
    an infusion device for moving particles from the source, through the separator, and into the vasculature of the patient; and
    an inflator for selectively configuring the balloon from a base configuration to a secondary configuration, wherein the balloon is deflated in the base configuration and inflated in the secondary configuration.

13. A system as recited in claim 12 wherein the proximal end of the separator is slanted at an angle "α" relative to the axis, with the distal end of the separator being substantially perpendicular to the axis.

14. A system as recited in claim 13 wherein a proximal end of each lumen in the separator is oriented substantially perpendicular to the axis of the catheter to establish a step configuration for the proximal end of the separator.

15. A system as recited in claim 12 wherein the balloon is positioned around the catheter at a location proximal the separator.

16. A system as recited in claim 12 wherein the particles are selected from a group consisting of agents useful for gene therapy, drug therapy and protein therapy.

17. A system as recited in claim 12 wherein the particles are stem cells.

18. A method for introducing particles into the vasculature of a patient, the method comprising the steps of:

provinding an elongated catheter defining an axis and having a proximal end and a distal end, wherein the proximal end of the catheter is connected in fluid communication with a source of the particles, and wherein the particles are suspended in a fluid;

connecting a substantially cylindrical shaped separator having a proximal end and a distal end in fluid communication with the particle source, wherein the separator is formed with a plurality of longitudinally aligned, parallel lumens, with each lumen in fluid communication with the central lumen to receive particles from the central lumen with each lumen dimensioned to receive particles therethrough, and wherein the separator is positioned in the catheter at a distance "d" from the distal end of the catheter to establish a recollection chamber, and further wherein a configurable balloon is positioned around the catheter and affixed thereto, with the balloon being extendable in a radial direction outward from the catheter to regulate axial movement of blood outside of the catheter in a direction substantially parallel to the axis of the separator;

positioning the separator in the catheter; and selectively inflating the balloon to control the flow rate of blood through the vasculature of a patient.

19. A method as recited in claim 18 wherein the proximal end of the separator is slanted at an angle "α" relative to the axis, with the distal end of the separator being substantially perpendicular to the axis.

20. A method as recited in claim 19 wherein a proximal end of each lumen in the separator is oriented substantially perpendicular to the axis of the separator to establish a step configuration for the proximal end of the separator.

* * * * *